US00PP11248P

United States Patent [19]

Churchus

[11] Patent Number: Plant 11,248

[45] Date of Patent: Feb. 29, 2000

[54] DOUBLE IMPATIENS PLANT NAMED 'GOLDEN GIRL'

[76] Inventor: John William Churchus, 4 Fiona Dr., Devon Meadows, Victoria 3977, Australia

[21] Appl. No.: 08/963,515

[22] Filed: Nov. 3, 1997

[51] Int. Cl.[7] ..... A01H 5/00

[52] U.S. Cl. ..... Plt./317

[58] Field of Search ..... Plt./87.6, 319, Plt./317

*Primary Examiner*—Howard J. Locker
*Assistant Examiner*—Anne Marie Grüberg
*Attorney, Agent, or Firm*—C. A. Whealy

[57] ABSTRACT

A new and distinct cultivar of Double Impatiens plant named 'Golden Girl', characterized by its unique and stable light yellow and green variegated foliage; large dark pink flowers; consistently double and symmetrical flower form; numerous flowers per plant; freely branching, dense and bushy plant habit; low-growing, outwardly spreading to cascading, and mounded plant habit; suitable for hanging baskets and patio containers; and excellent landscape performance.

1 Drawing Sheet

The present invention relates to a new and distinct cultivar of Double Impatiens plant, botanically known as *Impatiens walleriana,* and hereinafter referred to by the cultivar name Golden Girl.

The new cultivar is a spontaneous branch mutation of the *Impatiens walleriana* cultivar Double Peach (not patented). The new cultivar was discovered and selected by the inventor in a controlled environment in Devon Meadows, Victoria, Australia in 1991, as a mutation of the upright and solid green leaf-colored cultivar Double Peach. Asexual reproduction of the new cultivar by terminal cuttings taken at Devon Meadows, Victoria, Australia, has shown that the unique features of this new Double Impatiens are stable and reproduced true to type in successive generations of asexual reproduction.

The following traits have been repeatedly observed and are determined to be the unique characteristics of 'Golden Girl'. These characteristics in combination distinguish the new Double Impatiens as a new and distinct cultivar:

1. Unique and stable light yellow and green variegated foliage.
2. Large dark pink flowers.
3. Consistently double and symmetrical flower form.
4. Numerous flowers per plant.
5. Freely branching, dense and bushy plant habit.
6. Low-growing, outwardly spreading to cascading, and mounded plant habit, suitable for hanging baskets and patio containers.
7. Excellent landscape performance.

The new Double Impatiens has not been observed under all possible environmental conditions. The phenotype may vary significantly with variations in environment such as temperature and light level, without, however, any variance in genotype.

BRIEF DESCRIPTION OF THE PHOTOGRAPHS

The accompanying colored photographs illustrate the overall appearance and flower color of the new Double Impatiens, showing the colors as true as it is reasonably possible to obtain in colored reproductions of this type.

The photograph at the top of the sheet comprises a top perspective view of a typical plant of the new Double Impatiens.

The photograph at the bottom of the sheet comprises a close-up view of typical leaves and flowers of the new Double Impatiens. Flower and foliage colors in the photographs may appear different from the actual colors due to light reflectance.

DETAILED BOTANICAL DESCRIPTION

The following observations, measurements, values, and comparisons describe plants grown under outdoor production conditions in 16.5-cm containers in Keller, Tex., in full and partial shade during the summer.

In the following description, color references are made to The Royal Horticultural Society Colour Chart except where general terms of ordinary dictionary significance are used.

Botanical classification: *Impatiens walleriana* cultivar Golden Girl.

Parentage: Spontaneous branch mutation of *Impatiens walleriana* cultivar Double Peach (not patented).

Propagation:

*Type cutting.*—Terminal cuttings.

*Time to initiate roots.*—Summer: About 7 days at a temperature of 15° C. Winter: About 14 days at a temperature of 10° C.

*Rooting habit.*—Numerous, strong, fine, and freely-branching.

Plant description:

*Form.*—Low-growing, outwardly spreading to cascading, and mounded plant habit. Freely branching, dense and bushy growth. Large flowers that face upright or outward.

*Usage.*—Suitable for 10 to 25-cm containers; recommended for hanging baskets and patio containers; excellent garden performance.

*Vigor.*—Moderate and moderate growth rate.

*Plant height.*—About 12.5 cm.

*Plant spread.*—About 42 cm.

*Branching habit.*—Freely branching with numerous lateral branches, branches very strong and flexible.

*Lateral branches.*—Length: About 16 cm. Diameter: About 7 mm. Internode length: About 1.75 cm. Color: Translucent, light green, close to 144C, with red-purple, 59A, spots that are most prevalent at nodes.

*Foliage description.*—Leaves simple, generally symmetrical, abundant, alternate, and flat in aspect. Length: About 4.5 cm. Width: About 3 cm. Shape: Ovate with acuminate apex, cuneate base and crenate margin. Texture: Smooth. Color: Light yellow and green variegated leaves; green at center with light yellow at margins. Actual shape and size of yellow and green areas is variable. Young leaves, upper surface: Yellow areas: 11A. Green areas: 146A/144A. Young leaves, lower surfaces: Yellow areas: 11A. Green areas: 146B with red (dulled 178A) spots/blotches. Fully expanded leaves, upper surface: Yellow areas: 10C/11B/11C/11D. Green areas: Close to 147B and lighter green areas, 147C. Fully expanded leaves, lower surface: Yellow areas: 11C/11D. Green areas: Close to 143C and 146B with red (dulled 178A) spots/blotches. Venation, upper surface: Similar to leaf surface color, 146B/146C, iridescent. Venation, lower surface: 146A. Petiole: Length: About 2 cm. Diameter: About 2 mm. Color: Very light green to white.

Flower description:

*Flower type and habit.*—Large dark pink flowers. Consistently double and symmetrical flowers. Freely and continuously flowering. Flower buds open similar to a rose in fullness. Flowers arise from leaf axils, terminal bud opening first. Usually three or four flowers per lateral branch. Flowers face upright or outward. Flowers self-cleaning.

*Time to flower.*—Flowering generally commences four to six weeks after planting.

*Flowering season.*—Year-round under greenhouse conditions. In the garden, flowering is continuous from spring until fall.

*Flower diameter.*—About 4 cm.

*Flower depth (height).*—About 2 cm.

*Flower buds.*—Length: About 1.3 cm. Diameter: About 9 mm. Shape: Ovoid. Color: 50C.

*Petals/petaloids.*—Quantity: Numerous, typically more than 15. Length: About 2 cm. Width: About 1.5 cm. Shape: Obovate with rounded apex, cuneate base and entire margin. Texture: Satiny, smooth. Color: When opening, upper surface: Iridescent, 51A, with purple, close to 57A , spot at base. When opening, lower surface: Iridescent, 51A. Mature, upper surface: Iridescent, 51B with fine darker pink streaks, close to 51A, and purple, close to 57A, spot at base. Mature, lower surface: Iridescent, 51C. Fading to: Iridescent, 51C.

*Spur.*—Length: About 3 cm. Shape: Narrow and curved. Color: Initially green, close to 144A, becoming light pink, close to 51B.

*Peduncles.*—Length: About 2.75 cm. Angle: Upright to outwardly arching. Strength: Moderate, flexible. Color: Glossy, translucent, light green.

*Reproductive organs.*—None observed. Under optimal flowering conditions, reproductive organs are not observed as these structures develop into sterile petaloids. Without the development of functional reproductive organs, pollination and subsequent seed production are not observed.

Disease resistance: Under commercial conditions, resistance to pathogens has not been observed.

It is claimed:

1. A new and distinct Double Impatiens plant named 'Golden Girl', as illustrated and described.

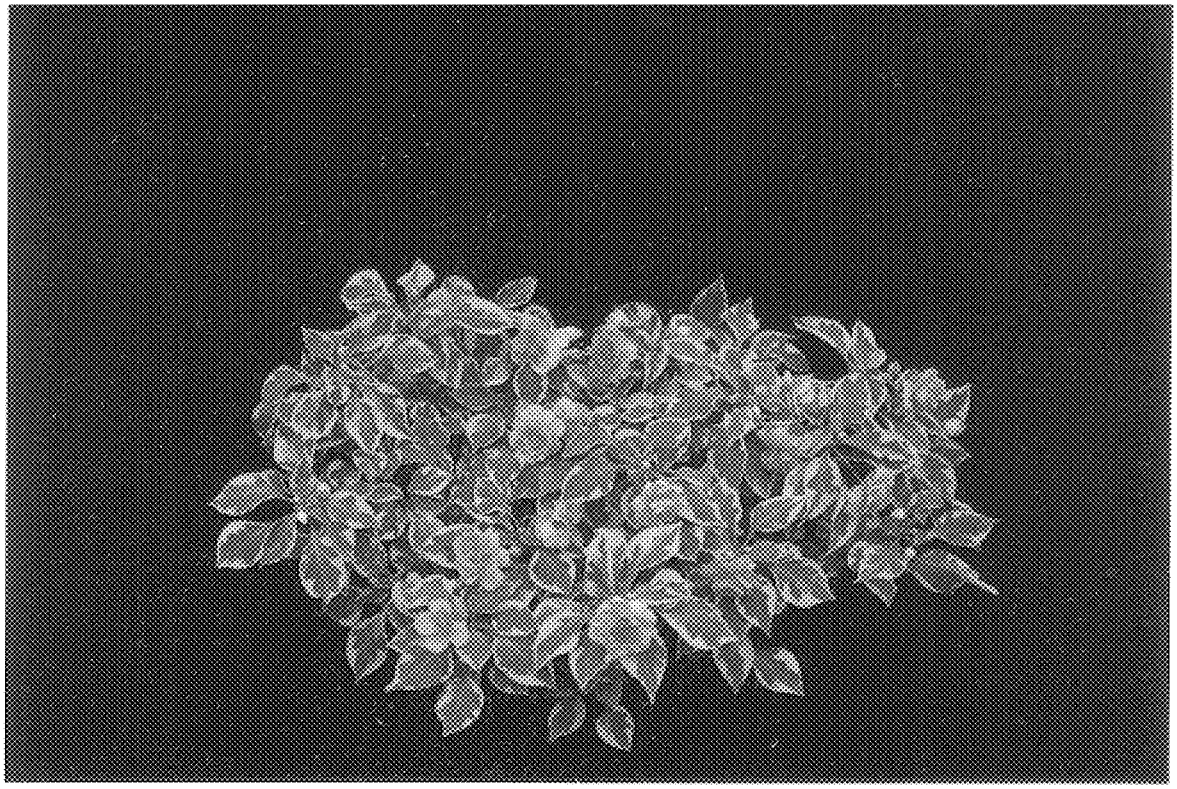
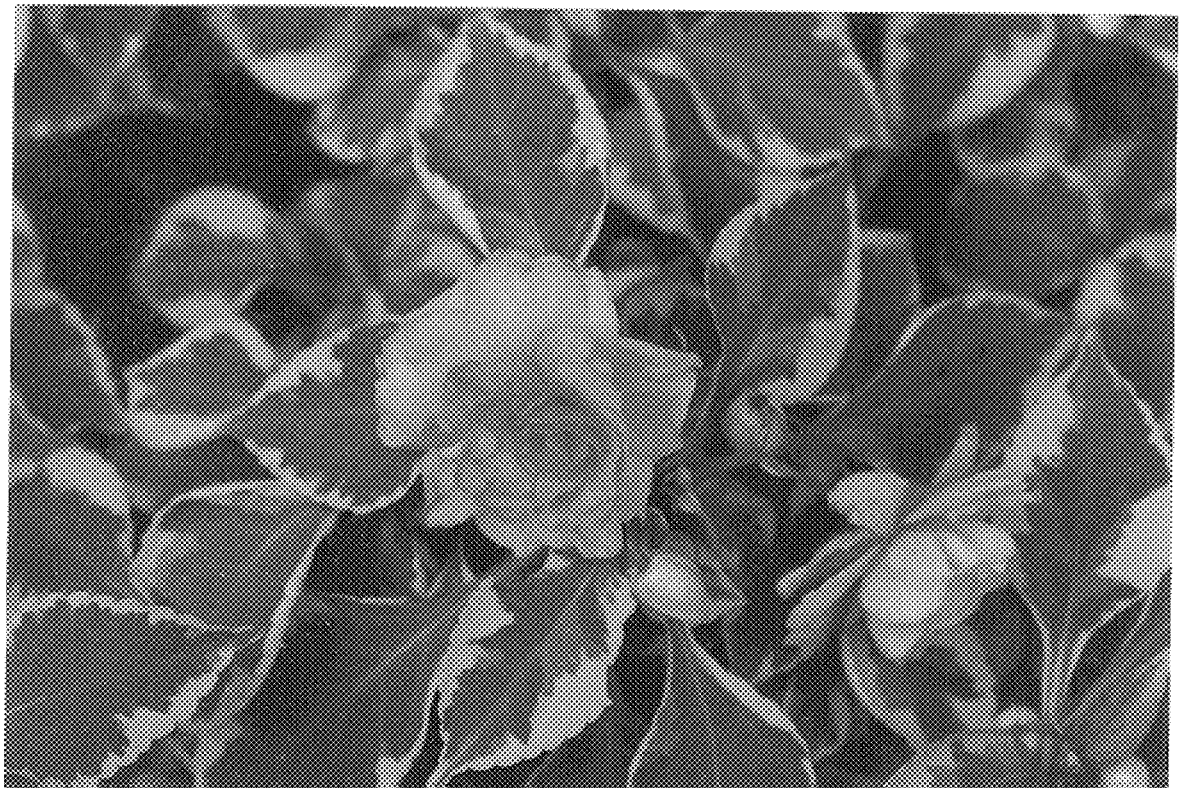

* * * * *